(12) United States Patent
Grotelüschen et al.

(10) Patent No.: US 7,872,049 B2
(45) Date of Patent: Jan. 18, 2011

(54) LONG-TERM STABLE PHARMACEUTICAL PREPARATION CONTAINING THE ACTIVE INGREDIENT GLYCERYL TRINITRATE

(75) Inventors: Rolf Grotelüschen, Aukrug (DE); Henning Ueck, Bekmünde (DE); Thomas Zimmeck, Hohenlockstedt (DE)

(73) Assignee: G. Pohl-Boskamp GmbH & Co. KG, Hohenlockstedt (DE)

( * ) Notice: Subject to any disclaimer, the term of this patent is extended or adjusted under 35 U.S.C. 154(b) by 0 days.

(21) Appl. No.: 12/789,217

(22) Filed: May 27, 2010

(65) Prior Publication Data

US 2010/0227922 A1    Sep. 9, 2010

Related U.S. Application Data

(63) Continuation of application No. 12/752,070, filed on Mar. 31, 2010, which is a continuation of application No. PCT/EP2009/001772, filed on Mar. 12, 2009.

(60) Provisional application No. 61/207,864, filed on Mar. 14, 2008.

(51) Int. Cl.
    *A61K 31/14* (2006.01)
(52) U.S. Cl. .................................. 514/645
(58) Field of Classification Search ............... 514/645
    See application file for complete search history.

(56) References Cited

U.S. PATENT DOCUMENTS

| 4,919,919 A | 4/1990 | Aouda |
| 5,186,925 A | 2/1993 | Cholcha |
| 5,744,124 A | 4/1998 | Klokkers-Bethke |
| 2003/0095925 A1 | 5/2003 | Dugger |
| 2004/0228883 A1 | 11/2004 | Karl |
| 2006/0003011 A1 | 1/2006 | Crew |
| 2007/0059346 A1* | 3/2007 | Maibach ..................... 424/443 |

FOREIGN PATENT DOCUMENTS

| DE | 202008007318 U1 | 9/2008 |
| WO | WO99/38472 | * 8/1999 |
| WO | 2007123955 | 11/2007 |

OTHER PUBLICATIONS

Nitrolingual Pumpspray product insert (nitroglycerin lingual spray), G. Pohl-Boskamp GmbH & Co. KG, Oct. 2008, 4 pages.
Nitrolingual Pumpspray package labelling (nitroglycerin lingual spray), G. Pohl-Boskamp GmbH & Co. KG, Nov. 2008, 1 page.
Nitrolingual Pumpspray bottle labelling (nitroglycerin lingual spray), G. Pohl-Boskamp GmbH & Co. KG, May 2006, 2 pages.

* cited by examiner

*Primary Examiner*—Ardin Marschel
*Assistant Examiner*—Nelson C Blakely, III
(74) *Attorney, Agent, or Firm*—K&L Gates LLP

(57) ABSTRACT

A pharmaceutical preparation containing the active substance glyceryl trinitrate having improved storage stability in a container. The improved storage stability is achieved by the addition of a proton-absorbing substance either as part of the preparation as placed into the container or applied to the surface of the preparation's storage container before the remaining components of the preparation are placed into the container. The preparation can preferably be filled into a plastic bottle having a spray pump.

7 Claims, 4 Drawing Sheets

LONG-TERM STABLE PHARMACEUTICAL PREPARATION CONTAINING THE ACTIVE INGREDIENT GLYCERYL TRINITRATE

This application is a continuation of U.S. patent application Ser. No. 12/752,070, filed Mar. 31, 2010, which is a continuation of International Application No. PCT/EP2009/001772, filed Mar. 12, 2009, which claims priority to and the benefit of U.S. Provisional Application No. 61/207,864, filed Mar. 14, 2008, the entire disclosures of each of which are incorporated by reference herein.

The invention concerns a pharmaceutical preparation with the active substance glyceryl trinitrate and is characterised by increased storage stability. The increased storage stability is achieved through a content of proton-absorbing substances in the preparation or on the surface of its storage container. The preparation can be filled and stored in a glass bottle or preferably in a plastic bottle with spray pump.

Glyceryl trinitrate (nitroglycerin, hereinafter also abbreviated to GTN) is an active substance for the treatment of angina pectoris attacks. It is used, for example, in emergency situations in which the pharmaceutical formulation must allow a rapid onset of action. Besides sublingual tablets, which however have a slower onset of action, especially bite capsules and sprays have proved successful in this specific indication. In the case of a spray, direct and rapid application of a solution of the active substance onto a large portion of the oral mucosa that readily absorbs the active substance GTN is advantageously assured by spraying the active substance-containing dose into the mouth.

Sprays containing GTN can be formulated with or without the addition of propellant gas. Sprays containing propellant gas are described for example in U.S. Pat. No. 3,155,574, in European Patent EP 0 461 505 and in German Published Patent Application DE 32 46 081. A GTN formulation without propellant gas to be presented as a pump spray is disclosed in EP 0 448 961.

GTN is a medium-polarity fluid that is readily soluble in a very large number of solvents except for water. Spray formulations can therefore be based on non-aqueous lipophilic, on non-aqueous but water-miscible or on polar, water-containing solvent mixtures. EP 0 448 961, for example, describes a rather lipophilic preparation with a preferred triglyceride content of 80% and ethanol as cosolvent in a concentration of 20%. The propellant gas spray according to the teaching of EP 0 927 032, which in addition to the propellant contains approx. 30% triglycerides, also exhibits a distinctly lipophilic nature. In contrast, the spray according to U.S. Pat. No. 3,155,574 contains in addition to the propellant 25% ethanol as solvent and can therefore be assigned to the $2^{nd}$ group of formulations. European Patent EP 0 471 161, finally, describes a pump spray containing 42% water as solvent in addition to ethanol and 1,2-propanediol. The active substance concentration of commercialised sprays is usually below 1%, since the dose needed to treat an angina pectoris attack is below 1 mg.

GTN is not a stable substance. Whereas as a pure substance it represents an explosion hazard and is used in the form of dynamite, solutions, for example in ethanol or medium-chain triglycerides, are less highly reactive. As a triple ester, however, GTN is readily hydrolysed both in the acidic and alkaline pH region. In pharmaceutical products, degradation reactions to 1,2- and 1,3-glyceryl dinitrate (GDN) and to 1- or 2-glyceryl mononitrate (GMN) are observed. These degradation reactions represent a limiting factor for the storage stability and shelf life of GTN sprays.

To date, commercialised GTN sprays have been filled into glass bottles. However, a lighter and shatter-resistant form of packaging, such as a plastic bottle, would be desirable since patients have to carry the spray with them at all times because angina pectoris attacks occur with an increased incidence especially during activities outside the home. Because of the instability of GTN, it has not been possible so far to develop a world-wide marketable GTN spray for the treatment of angina pectoris attacks packed in a plastic bottle.

However, if commercially available glass bottles are used, stability problems have been observed, too. It is attempted to ensure that pharmaceutical preparations also remain stable during storage at elevated temperatures. For example, the internationally applicable rules prescribe the performance of stress tests, i.e. storage of the preparation at 40° C. over a period of six months. For export to warmer countries, monitoring of the active substance content over the entire proposed shelf life period is to be performed at a storage temperature of 30° C. There is therefore a need for GTN-containing preparations of increased storage stability.

One object of the invention is therefore to provide a storage-stable preparation with the active substance GTN.

Another object of the invention is to provide a storage-stable preparation with the active substance GTN in a plastic bottle.

These objects are attained by the features of the independent claims. The dependent claims define advantageous embodiments of the invention.

Figure 1:
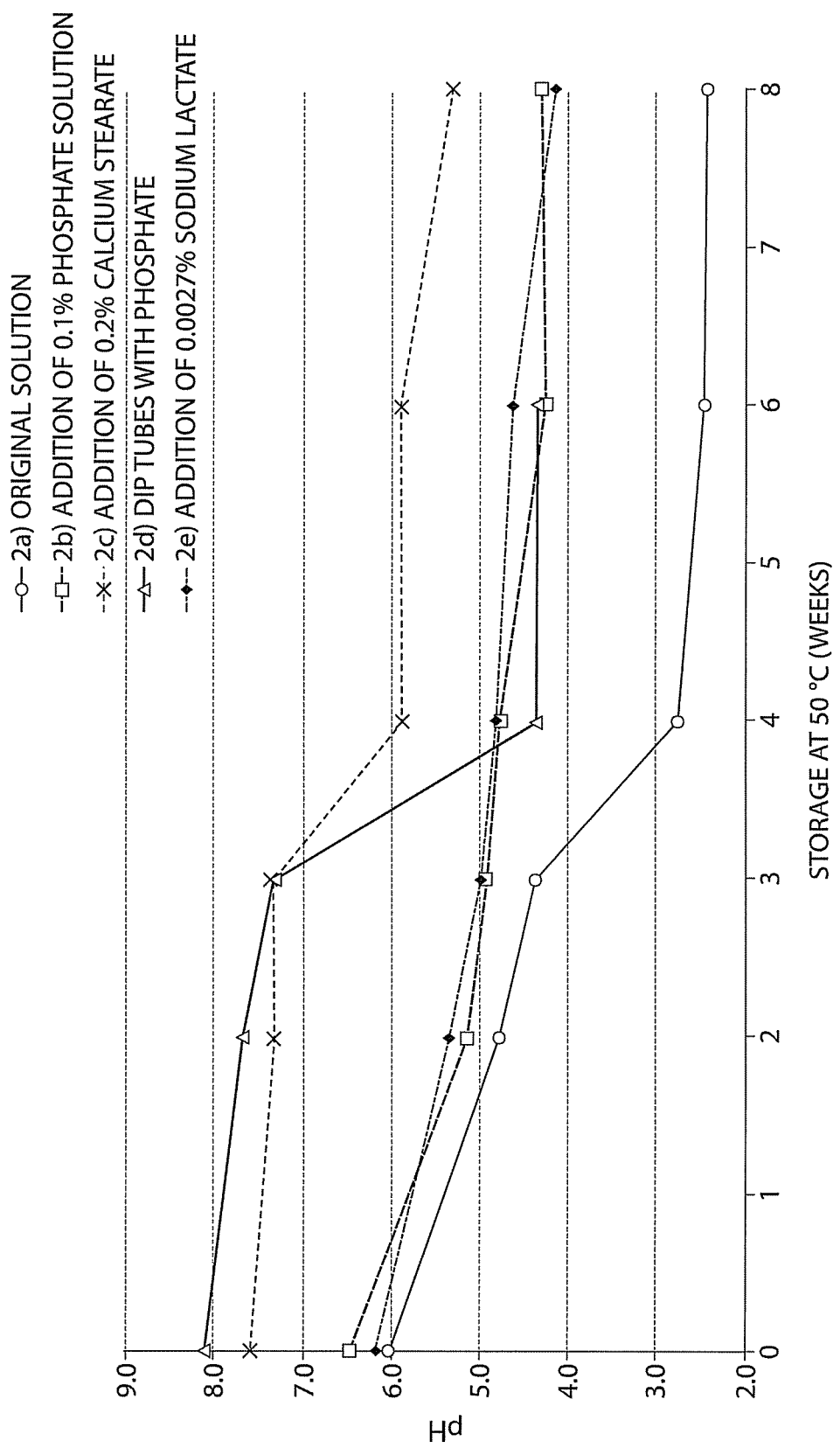
FIG. 1 is a graph showing pH value decrease in buffered solutions and in solutions without buffer in plastic bottles.

The investigations underlying the present invention that were performed on a GTN spray according to the formulation described in EP 0 448 961 showed that a saltatory increase in the degradation products 1,2-GDN, 1,3-GDN and GMN occurs after a certain storage period at elevated temperature (40° C. or 50° C.). Further investigations have shown that these degradation processes proceed more rapidly in plastic bottles. The experiments performed are explained in greater detail below in Comparison Example 1.

It is assumed that after a certain storage period traces of acids, especially nitric acid, are formed which accelerate the degradation process in an autocatalytic manner. This is proved by the fact that inorganic nitrate is detectable by test stick in stored samples and that appreciable amounts of acid can be extracted with water.

It is assumed that the glass surface is able to absorb protons that form in the initial phase of degradation of the GTN and in this way is able to improve the stability of the product. Since the buffer capacity of the glass is limited, however, and moreover may vary depending on the batch, there is a need for improvement in the storage stability of the compositions both for the commonly used glass bottles and for plastic bottles.

It has now surprisingly been found that, despite the alkali sensitivity of GTN, the addition of small amounts of proton-absorbing or proton-buffering substances can considerably improve the stability of a GTN preparation. The object of the invention is therefore attained by using such proton-absorbing materials in the solution or on the packaging materials with which it is in direct contact. The following preferred examples of embodiment are possible:

Dissolution of the substance in the GTN preparation

Addition of the finely dispersed undissolved substance

Application of the substance to a surface which is in contact with the GTN-containing preparation, for example onto the inside surface of the bottle or the dip tube of the spray device.

The following examples explain the invention further and prove the shelf life prolonging effect of the proton-absorbing additives. However, they are not to be understood as restricting the invention to these examples of embodiment. An expert will readily be able to develop other examples of embodiment according to the teaching presented above.

Comparison Example 1

Comparative Stability Studies in Plastic Bottles and Glass Bottles (Stability Storage at 40° C.)

For 1 kg spray solution, 166 g GTN in medium-chain triglycerides (5% solution), 607 g medium-chain triglycerides, 7.2 g peppermint oil, 200 g absolute ethanol and 20 g medium-chain partial glycerides are weighed out and intimately mixed. The solution is filled in portions of 12 g into either plastic or glass bottles with a nominal volume of 20 ml, closed with a spray pump and stored at 40° C. Samples are taken at three monthly intervals and assayed for partial nitrates by HPLC. For this purpose a test solution is prepared by weighing approx. 960 mg spray solution to an accuracy of 0.1 mg into a 10 ml volumetric flask and making up to the mark with methanol (equivalent to about 0.8 mg glyceryl trinitrate/ml).

The standard solution is prepared by adding 2.4 g placebo solution to 0.2 ml of a reference solution containing 0.5 mg GMN, 0.5 mg GDN-1,2 and 0.5 mg GDN-1,3 per ml methanol in a volumetric flask and diluting to 25.0 ml with methanol (in each case equivalent to approx. 0.004 mg related substance/ml). The placebo solution is prepared by weighing 77.3 g medium-chain triglycerides, 0.7 g peppermint oil, 20.0 g absolute ethanol and 2.0 g medium-chain partial glycerides into a suitable, closable vessel and homogenising.

Chromatography is performed on an RP 18 column with water/methanol 70/30 (V/V) as mobile phase and UV detection at a wavelength of 205 nm. The retention times of the partial nitrates are between 2 and 5 minutes. Quantitation is performed by the external standard method. The results are expressed in % with reference to GTN.

The following table shows the test results obtained with several exemplary batches.

| Batch/bottle material* | Initial value | 3 months 40° C.** | 6 months 40° C.** | 9 months 40° C.** |
|---|---|---|---|---|
| Formation of 1,2-glyceryl dinitrate (1,2-GDN) | | | | |
| X180/G | 0.04% | 0.09% | 0.16% | 1.64%\*** |
| X974/G | <0.03% | 0.10% | 0.92% | |
| X752/G | <0.03% | 0.16% | 1.59% | |
| X484/P | 0.04% | 0.08% | 3.32% | |
| X485/P | 0.03% | 2.30% | | |
| X486/P | 0.03% | 2.60% | | |
| Formation of 1,3-glyceryl dinitrate (1,3-GDN) | | | | |
| X180/G | 0.06% | 0.14% | 0.23% | 1.37% |
| X974/G | 0.05% | 0.15% | 0.71% | |
| X752/G | 0.07% | 0.24% | 1.33% | |
| X484/P | 0.06% | 0.09% | 2.61% | |
| X485/P | 0.06% | 1.61% | | |
| X486/P | 0.06% | 1.77% | | |

*G = glass, P = plastic
**The bottles are stored upright and inverted (upside down), respectively; the data for inverted storage are presented as examples.
***Out of specification values which resulted in termination of storage are shown in bold print.

Example 2

Addition of Stabilising Substances to a GTN-Containing Preparation in Plastic Bottles (Stress Test 50° C.)

The following solutions were prepared and subjected to stability tests:

Test solution 2a: Approx. 12 g spray solution according to Comparison Example 1 were filled into a plastic bottle of 20 ml nominal volume and the bottle was closed.

Test solution 2b: 0.10 g of a solution of 200 g/l disodium hydrogen phosphate dihydrate was added to 99.9 g spray solution according to Comparison Example 1, vigorously shaken, filled in portions of approx. 12 g into plastic bottles of 20 ml nominal volume and the bottles were closed.

Test solution 2c: 15-25 mg calcium stearate and approx. 12 g spray solution according to Comparison Example 1 were weighed into plastic bottles of 20 ml nominal volume. The bottles were closed and shaken; the calcium stearate, however, did not dissolve completely.

Test solution 2d: Pump dip tubes were immersed in a solution of 500 g/l disodium hydrogen phosphate dihydrate and dried on air overnight. Differential weighing showed that approx. 10 mg of the phosphate salt had precipitated out on the surface. The dip tubes were placed in plastic bottles of 20 ml nominal volume, approx. 12 g spray solution according to Comparison Example 1 were added to each bottle and the bottles were closed.

Test solution 2e: 2505 g of spray solution according to Comparison Example 1 are mixed with 0.134 g of an aqueous solution of sodium lactate having a concentration of 500 g/l and intimately mixed. About 12 g of this solution were filled into a plastic bottle of 20 ml nominal volume of and the bottles were closed.

The bottles were stored at 50° C., samples were taken weekly and the following parameters were investigated:

1. pH:

5 g solution are extracted with 1 g water and the pH of the aqueous phase is determined. The results are summarised in FIG. 1. Since the pH cannot be determined in the nearly anhydrous spray preparation, in this document the term "pH" is to be understood to mean the pH value determined in the manner described.

Figure 2:
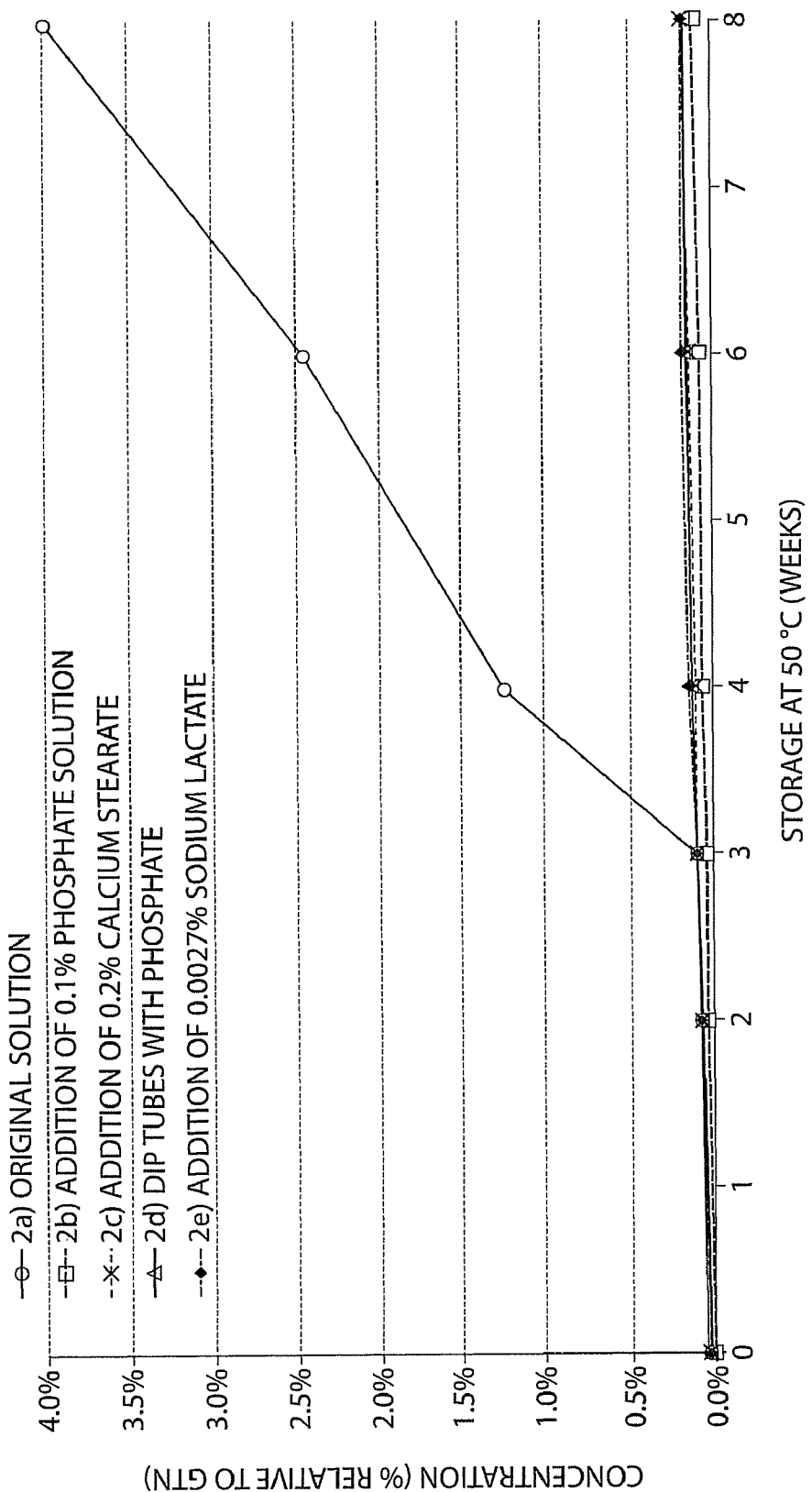
FIG. 2 is a graph showing formation of 1,2-GDN in buffered and non-buffered solutions in plastic bottles.

2. Determination of Partial Nitrates (Including 1,2-GDN) in Spray Solutions:

Method as described in Comparison Example 1. The results of the tests are summarised in FIG. 2.

For all the parameters investigated, marked differences are observed between the solutions with proton-absorbing substances and the original solution: The pH of the original solution decreases rapidly in the $4^{th}$ week and large amounts of the partial nitrate 1,2-GDN form. In the preparations according to the invention, the pH remains above the critical limit of 4.0 and there is no or only a very slight increase in the partial nitrates.

Example 3

Addition of Stabilising Substances to a GTN-Containing Preparation in Glass Bottles (Stress Test 50° C.)

The following solutions were prepared and subjected to stability tests:

Test solution 3a: Approx. 12 g spray solution—prepared according to Comparison Example 1—were filled without additives into a glass bottle of Hydrolytic Class III and the bottles were closed.

Test solution 3b: 0.25 g of a solution of 200 g/L disodium hydrogen phosphate dihydrate was added to 99.75 g spray solution according to Comparison Example 1, shaken vigorously, filled in portions of approx. 12 g into glass bottles of Hydrolytic Class III and the bottles were closed.

Test solution 3c: Approx. 12 g spray solution—prepared according to Comparison Example 1—were filled without additives into a glass bottle of Hydrolytic Class I and the bottles were closed.

Test solution 3d: 0.25 g of a solution of 200 g/L disodium hydrogen phosphate dihydrate was added to 99.75 g spray solution according to Comparison Example 1, shaken vigorously and filled in portions of approx. 12 g into glass bottles of Hydrolytic Class I and the bottles were closed.

Figure 3:
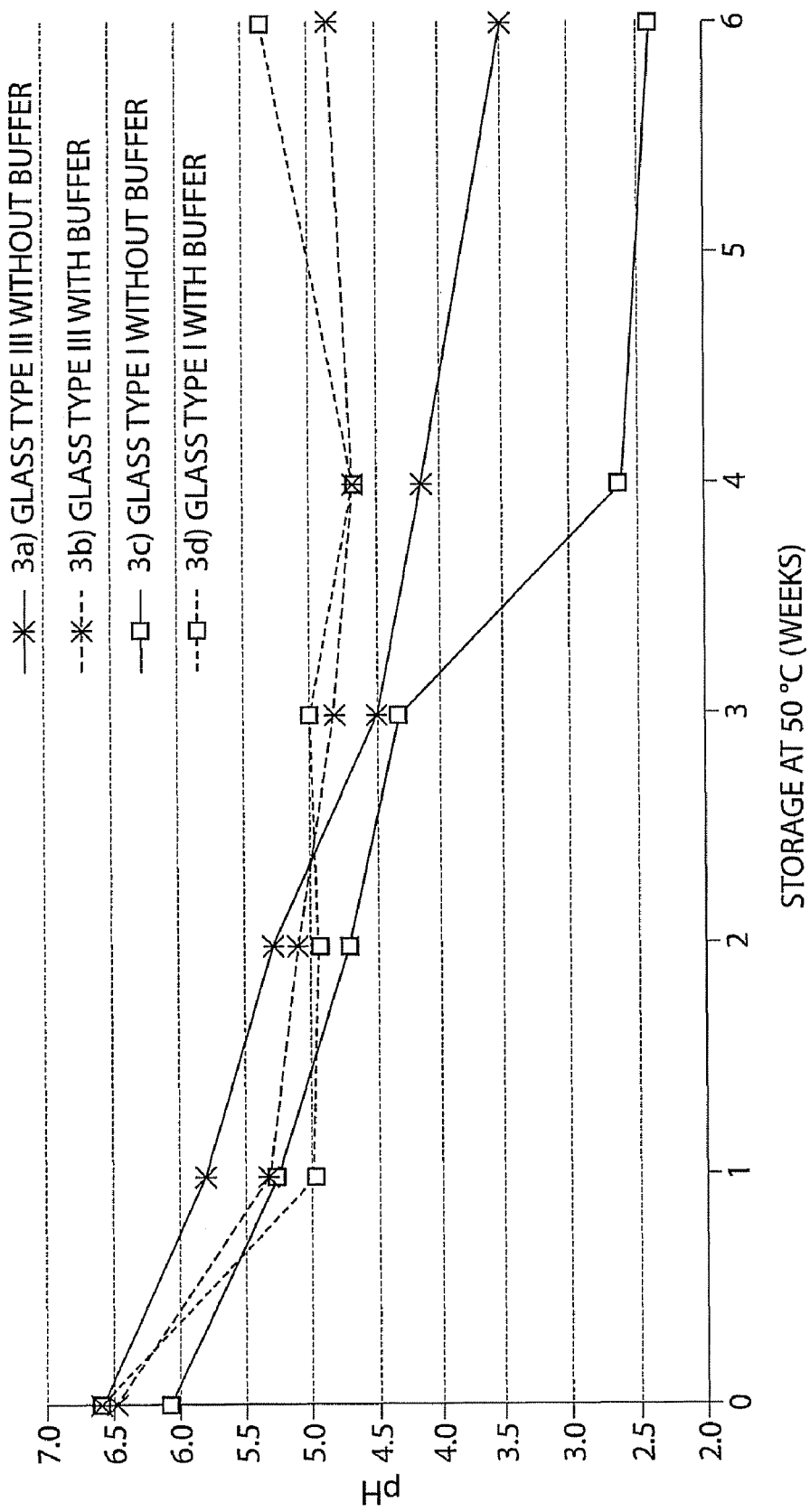
FIG. 3 is a graph showing pH value decrease in buffered solutions and in solutions without buffer in glass bottles.
Figure 4:
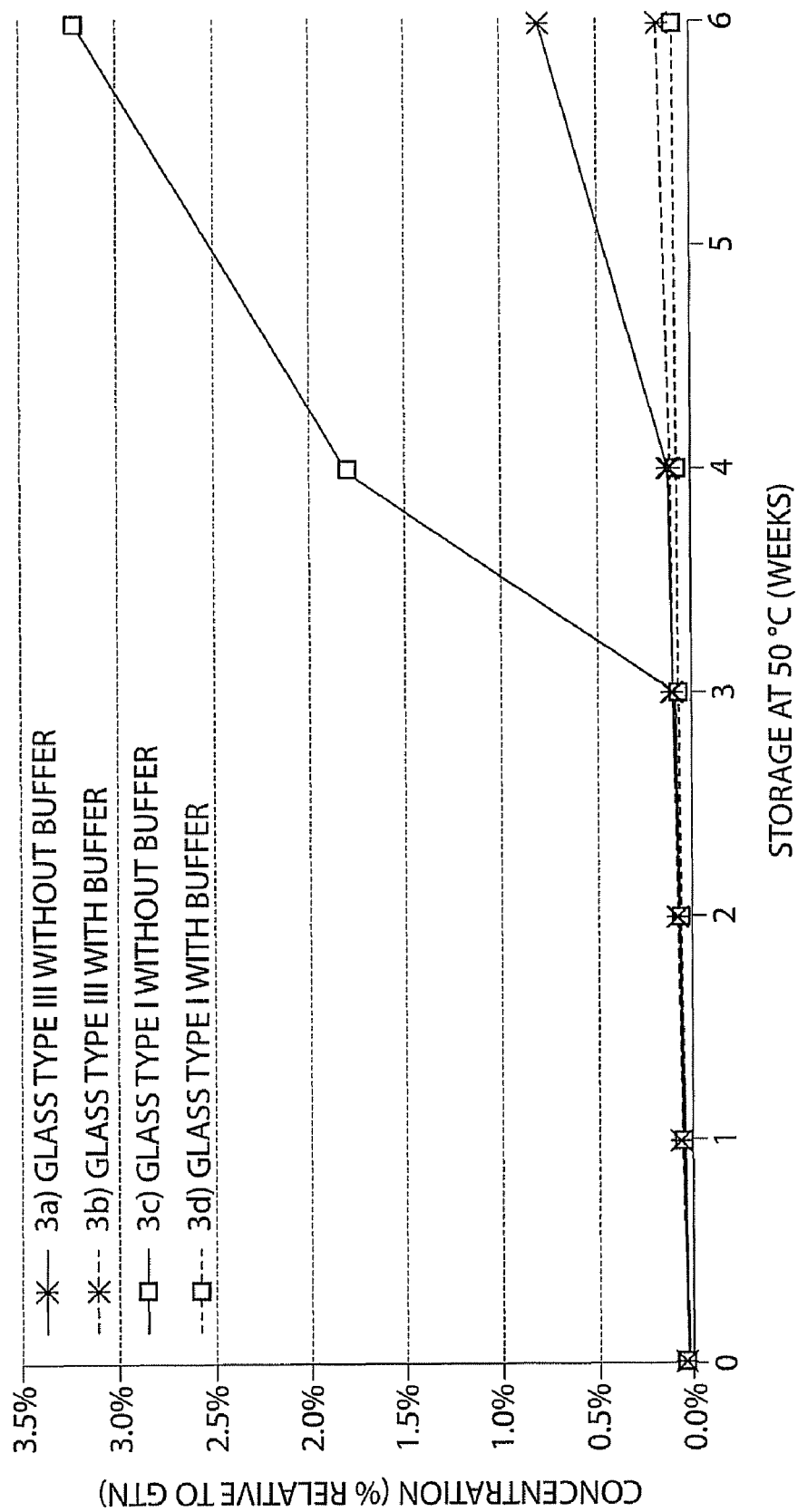
FIG. 4 is a graph showing formation of 1,2-GDN in solutions with and without a buffering substance in glass bottles.

The bottles were stored at 50° C., samples were taken weekly and the pH and the content of 1,2-GDN were measured in the same manner as described in Example 2. The results obtained are presented in FIGS. 3 and 4.

Without addition of a buffer substance, a marked decrease in pH and a substantial rise in the concentration of 1,2-glyceryl dinitrate are seen after 4 weeks in bottles of Glass Type I. In the bottles of Type III glass the pH decreases more slowly. In this case the pH does not fall below the critical level of 4.0 until after six weeks. The degradation product 1,2-GDN forms in smaller amounts. These results are consistent with the hypothesis that proton-adsorbing substances have a stability prolonging effect, since glasses of Hydrolytic Class I, in contrast to those of Hydrolytic Class III, undergo surface treatment that reduces their basicity. With both types of glass, the addition of a buffer substance results in the desired stability over the period of six weeks.

Example 4

Addition of Sodium Lactate to a GTN-Containing Preparation in Plastic Bottles (Storage at 40° C.)

The following solutions were prepared and subjected to a stability test:

Non-stabilized solution: Approx. 12 g spray solution according to Comparison Example 1 are filled into a plastic bottle of 20 ml nominal volume and the bottle was closed.

Stabilized solution: 2501 g spray solution according to Comparison Example 1 are mixed with 0.457 g of an aqueous solution of sodium lactate having a concentration of 500 g/l and shaken vigorously. Portions of about 12 g of this solution were filled into plastic bottles of 20 ml nominal volume and the bottles were closed.

The bottles were stored at 40° C., samples were taken after 6 months and the pH-value as well as the concentrations of the degradation product 1,2-GDN were determined as described above:

|  | Stabilized solution | | Non-stabilized solution | |
| --- | --- | --- | --- | --- |
|  | pH-value | 1,2-GDN | pH-value | 1,2-GDN |
| Initial value | 6.40 | 0.05% | 5.96 | 0.04% |
| After 6 months at 40° C. | 4.97 | 0.12% | 1.87 | 4.49% |

In the course of a pharmaceutical development, a stability study under accelerated conditions, i.e. at a storage temperature of 40° C. over a period of at least 6 months is required. The obtained data confirm that the addition of proton absorbing substances reduces the degradation reaction of GTN to a minimum level. As demonstrated above, this product is stable at 40° C. in contrast to the non-stabilised solution.

The compositions according to the invention contain preferably 0.1-10% by weight, particularly preferably 0.2-5% by weight (such as 0.6, 0.7, 0.8, 0.9 or 1.0% by weight) glyceryl trinitrate, with reference to the composition.

GTN preparations according to the invention generally contain less than 5% water, preferably less than 0.5% water. As solvents for the active substance, triglycerides of plant or semi-synthetic origin, physiologically compatible alcohols and polyalcohols may be used, preference being given to triglycerides, ethanol, propylene glycol and mixtures of these components. Preferred are triglycerides, whose fatty acid fraction consists of saturated $C_8$ to $C_{12}$ fatty acids named as MIGLYOL® type, e.g., MIGLYOL® 810 or MIGLYOL® 812. Particularly preferred is a mixture of triglycerides and ethanol in the mixing ratio of 10 to 90 to 90 to 10. In addition, surfactants, flavouring agents and other commonly used pharmaceutical excipients may be included.

The GTN preparations according to the invention contain at least one buffer substance. The buffer substance should be contained in a sufficient but the smallest possible amount. If the buffer substance is added to the solution, amounts of less than 0.5% with reference to the weight of the preparation are preferred; particularly preferred are amounts from 0.001% to 0.2 weight %, such as 0.02, 0.03, 0.04, 0.05, 0.06, 0.07, 0.08, 0.09 or 0.1 weight %. If the buffer substance is applied to the surface of the packaging components in contact with the product, amounts of less than 0.2% with reference to the weight of the preparation are preferred, such as 0.02, 0.03, 0.04, 0.05, 0.06, 0.07, 0.08, 0.09 or 1.0 weight %. The buffer substance can in particular be applied to the inside surface of the bottle and the parts of the spray pump in contact with the product. In the latter case, application to the dip tube is especially preferred.

If several buffer substances are used, the amounts mentioned above are the preferred total quantities.

The buffer substance is preferably selected such that it can adsorb protons in the pH region below 7. Preferred are buffer substances from the group of physiologically compatible salts of organic acids, the physiologically compatible salts of polymeric anions and/or the physiologically compatible salts of inorganic acids such as phosphoric and silicic acid, such as sodium stearate and calcium stearate, the sodium salt of hydroxypropylmethyl cellulose acetate succinate, the sodium salt of polyacrylate, polymethacrylate or carboxymethyl cellulose, di sodium monohydrogen phosphate, sodium phosphate or sodium lactate. Especially preferred are the buffer substances giving a weakly alkaline reaction in aqueous solution. In preferred embodiments the buffer substance is sodium lactate, disodium monohydrogen phosphate or calcium stearate; particularly preferred are disodium monohydrogen phosphate and/or sodium lactate.

The preparations according to the invention can be filled in usual plastic or glass containers which are equipped with usual dosing devices. Particularly preferred are dosing devices, which deliver 50 to 100 µl of the preparation per single spray puff.

Examples 5-9

The following table shows examples of preferred embodiments of compositions according to the invention. The preparations were made according to the method disclosed in Comparison Example 1.

| Contained substance* | Example 5 | Example 6 | Example 7 | Example 8 | Example 9 |
|---|---|---|---|---|---|
| Glyceryl trinitrate | 8.3 mg | 8.3 mg | 8.3 mg | 8.3 mg | 8.3 mg |
| Medium-chain triglycerides | 763.5 mg | 762.0 mg | 763.0 mg | 762.5 mg | 223.0 mg |
| Ethanol | 200.0 mg | 200.0 mg | 200.0 mg | 200.0 mg | 760.9 mg |
| Medium-chain partial triglycerides | 20.0 mg | 20.0 mg | 20.0 mg | 20.0 mg | — |
| Peppermint oil | 7.2 mg | 7.2 mg | 7.2 mg | 7.2 mg | 7.3 mg |
| Disodium monohydrogen phosphate | 1.0 mg** | 0.5 mg*** | — | 0.2 mg*** | 0.5 mg** |
| Sodium lactate | — | — | 0.1 mg# | 0.05 mg# | — |

*quantities are stated in mg/g preparation
**added as a solid
***added as a 20% aqueous solution. As a result, the preparation contains approx. 0.2 and 0.08% water respectively
added as 50% solution

The invention claimed is:

1. A pharmaceutical preparation consisting essentially of: glyceryl trinitrate in a quantity between about 0.2% and about 5% w/w; a triglyceride and an alcohol, wherein the triglyceride and the alcohol are mixed in a ratio of about 10:90 to about 90:10; a buffer selected from the group consisting of: pharmaceutically acceptable salts of lactic acid, phosphoric acid, and stearic acid, in a quantity less than about 0.5% w/w; water in a quantity less than about 5.0% w/w; a medium-chain partial glyceride, and a flavoring agent; wherein the pharmaceutical preparation is in the form of an oral spray solution.

2. The preparation according to claim 1, wherein the buffer is sodium lactate, disodium monohydrogen phosphate, sodium phosphate, or calcium stearate.

3. The preparation according to claim 1, wherein the preparation contains water in a quantity less than about 0.5% w/w.

4. The preparation of claim 1, wherein the triglyceride is a medium-chain triglyceride, a triglyceride of plant or semi-synthetic origin, a saturated $C_8$ to $C_{12}$ fatty acid triglyceride, or a combination of any two or more of the foregoing.

5. The preparation of claim 1, wherein the alcohol is a physiologically compatible alcohol, a polyalcohol, propylene glycol, ethanol, absolute ethanol, or a combination of any two or more of the foregoing.

6. The preparation of claim 1, wherein the glyceryl trinitrate is provided in an effective dose to treat angina pectoris when delivered using a pump spray.

7. The preparation of claim 1, wherein the triglyceride is in a quantity between about 10% and about 80% w/w and the alcohol is in a quantity between about 10% and about 80% w/w.

* * * * *